United States Patent [19]

Jovanovics et al.

[11] 4,279,816
[45] Jul. 21, 1981

[54] N-FORMYL LEUROSINE DERIVATIVES IN A DOSAGE FORM EFFECTIVE FOR TREATING LYMPHOID LEUKEMIA

[75] Inventors: Karola Jovánovics; Kálmán Szász; Bela Kellner; László Németh; Zsuzsa Relle; Emil Bittner; Eszter Dezséri; János Éles, all of Budapest, Hungary

[73] Assignee: Richter Gedeon Vegyszeti Gyar Rt., Budapest, Hungary

[21] Appl. No.: 547,374

[22] Filed: Feb. 5, 1975

Related U.S. Application Data

[62] Division of Ser. No. 422,100, Dec. 5, 1973, Pat. No. 4,189,432.

[51] Int. Cl.³ ................. C07D 519/04; A61K 31/475
[52] U.S. Cl. .................................. 260/244.4; 424/262
[58] Field of Search ........................ 260/287 B, 244.4

[56] References Cited

U.S. PATENT DOCUMENTS 3,387,001  6/1968  Hargrove et al. ............... 260/287 B

OTHER PUBLICATIONS

"Cancer Chemotherapy Reports," vol. 1, pp. 10-13 (1959).

Primary Examiner—Donald G. Daus
Assistant Examiner—Diana G. Rivers
Attorney, Agent, or Firm—Karl F. Ross

[57] ABSTRACT

New leurosine derivatives of the general formula (1),

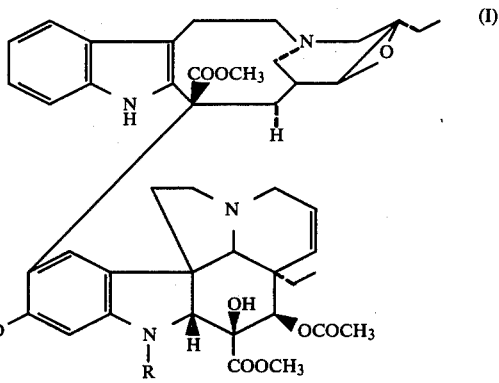

wherein R stands for hydrogen or formyl, or pharmaceutically acceptable acid addition salts thereof were prepared by oxidizing leurosine or an acid addition salt thereof, optionally formylating the thus-obtained product and then separating, and, if desired, converting any of the free bases into its acid addition salt.

2 Claims, No Drawings

N-FORMYL LEUROSINE DERIVATIVES IN A DOSAGE FORM EFFECTIVE FOR TREATING LYMPHOID LEUKEMIA

This is a division of application Ser. No. 422,100, filed Dec. 5, 1973, now U.S. Pat. No. 4,189,432.

This invention relates to a method of treatment using pharmaceutically active leurosine derivatives of the formula (I),

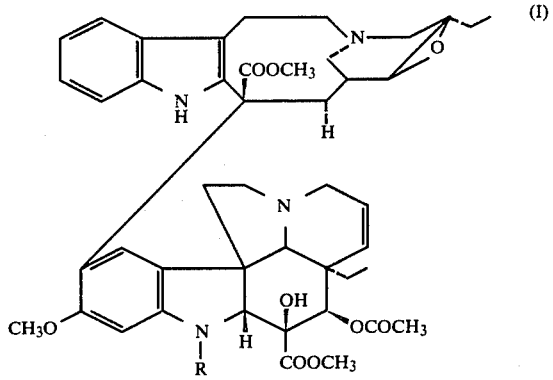

wherein R is hydrogen or a formyl group, as well as to a process for the preparation thereof.

In the last decades very intensive research has been carried out on the production of medicaments usable for the treatment of cancer. During this far-reaching research work substances with most diverse chemical structures have been subjected to biological and clinical investigations, but only a very limited number of these substances have proven to be curative in human therapy. Of these few pharmaceutical products, which show positive results in the clinical practice, the diindole alkaloids (dimeric indole alkaloids) proved to be outstandingly important. Such diindole alkaloids are, for instance, vincaleucoblastine (vinblastine), leurocristine (vincristine), vinleurosidine (leurosidine), vinleurosine (leurosine), etc. All of these compounds were prepared, as a result of extensive research, from the plant Cathareanthus roseus G. Don (or Vinca rosea l.), belonging to the family of Apocynaceae. These diindole alkaloids amount to about 1 to 3% of the total alkaloid content of the plant, which contains more than seventy individual alkaloids. It has been found by structural analysis that the diindole alkaloids have closely related structures, thus, for example, vinblastine and vinebristine molecules each contain one part of a velbanamine structure and another part containing a vindoline skeleton; the only difference being that the vindoline moiety of the molecule contains an N-methyl group in vinblastine, and an N-formyl group in vincristine. This minor structural difference causes, however, a significant difference in the biological activities of these compounds; namely, vineristine has proven to be more active both in animal tests, and, primarily, in the human therapy.

Leurosine is different in structure from the above-mentioned vinblastine or vincristine in so far as it contains an epoxy-velbanamine moiety in place of velbanamine.

The diindole alkaloids mentioned above, and their acid addition salts, as well as the preparation of these compounds have been described in many publications, of which U.S. Pat. Nos. 3,097,137, 3,205,220, and 3,225,030, and Hungarian Patent Specifications Nos. 153,200, 154,715 and 160,967 are mentioned.

In our experiments on the oxidation of leurosine we have found, unexpectedly, that leurosine can be oxidized in a fast reaction and with good yields into two compounds, namely into N-formyl-leurosine and N-demethyl-leurosine. If desired, N-demethyl-leurosine can be converted into N-formyl-leurosine by known formylation methods.

N-formyl-leurosine and N-demethyl-leurosine are hitherto unknown, new compounds.

Accordingly, this invention relates to a novel and pharmaceutically active compound of the general formula (I), or acid addition salts thereof—wherein R stands for hydrogen or formyl.

This invention relates further to a process for the preparation of a compound of the general formula (I), or the acid addition salts thereof—wherein R stands for hydrogen or formyl—in which leurosine or an acid addition salt thereof is oxidized, the thus-obtained product is optionally formylated and then separated, and, if desired, any of the thus-obtained free base is converted into its acid addition salt.

N-formyl-leurosine is a compound with an $LD_{50}$ value of 28.8 mg./kg. (i.p., on mice), accordingly this compound is about five times less toxic than vinblastine, and about ten times less toxic than vincristine.

This compound provides complete recovery or a 300 percent extension of life span in 50 to 70 percent of the cases, in tests on mice inoculated with Ehrlich ascites carcinoma or NK/Ly lymphoma.

The treatment extends the life span of animals suffering from L-1210 lymphoid leukemia, s37 ascites sarcoma or Yoshida ascites sarcoma by about 150 to 250 percent. When injected subcutaneously, this compound inhibits by 70 to 80 percent the growth of transplanted solid tumours (Guerin carcinoma, S-180 sarcoma). The compound of the invention causes a remarkable growth inhibition on several tumours (e.g. on Harding Passey melanoma, VX rabbit lapham carcinoma, induced and transplanted rhabdomyo-sarcoma) which could hardly be treated, if at all, with the hitherto known cytostatics, also including vinblastine and vincristine.

In animal tests this compound can be administered in a dosis of 0.3 to 5.0 mg./kg. for prolonged periods without causing side-effects characteristic of and unavoidable with the known vinca-alkaloids. The therapeutical range of this alkaloid, is, accordingly, somewhat similar to that of vincristine, and about four times broader than that of vinleurosine.

The process of the invention consists in the following steps: leurosine, obtained by the chromatographical separation of the diindole alkaloids of the plant Cathranthus roseus G. Don, or a salt thereof, preferably the sulfate, is dissolved in an organic solvent or solvent mixture, preferably in a mixture of acetone and glacial acetic acid, the solution is cooled to a temperature below 0° C., preferably to −30° to −90° C., chromic acid or a chromate salt, dissolved in an organic solvent of the same temperature, preferably in acetic anhydride, is added to the above solution under intensive stirring and cooling, and the reaction mixture is allowed to stand for 5 to 15 minutes, preferably for 8 minutes. Then the reaction mixture is treated carefully with cold (−40° to −50° C.) aqueous ammonia to adjust the pH to 8 to 9, the mixture is diluted with water, and extracted with several portions of an organic solvent, preferably methylene chloride, until no alkaloid is present. The extracts are combined, washed with water, dried, and evaporated to dryness under reduced pressure. A white, foam-like, amorphous dry residue is obtained, which consists mainly of N-formyl-leurosine and N-demethyl-leurosine. These compounds are separated from each other by chromatography, using a column filled with aluminum oxide (IV-V activity grade). The filling is prepared from a benzene suspension of alumina. The first eluant is benzene, and the subsequent eluants are the mixtures of benzene with different amounts of a chlorinated hydrocarbon, preferably chloroform. The substances present in the various effluent fractions are identified by thin layer chromatography. First the accompanying substances leave the column, then N-demethyl-leurosine, and finally N-formyl-leurosine is eluted. The fractions containing identical substances are combined, evaporated to dryness under reduced pressure, and, if desired, the obtained bases are converted into their acid addition salts, preferably into the corresponding monosulfates. The compounds can be purified by recrystallization, if desired. This purification method is applied primarily on the salts. N-Demethyl-leurosine can be formylated by known methods (see C. W. Huffman: J. Org. Chem. 23, 727 /1958/) to yield N-formyl-leurosine.

According to a preferred methol of the invention one proceeds as follows: the dry residue, obtained in the processing of the reaction mixture of oxidation, is formylated with a mixture of formic acid and acetic anhydride. In this reaction N-demethyl-leurosine is converted into N-formyl-leurosine. The reaction mixture is neutralized, extracted with methylene chloride, the extract is washed with water, and evaporated to dryness under reduced pressure. The obtained dry residue is purified by chromatography. The obtained N-formyl-leurosine is converted optionally into its salt, preferably into the sulfate, and the salt is recrystallized, if desired.

The invention is elucidated in detail in the following non-limiting Examples.

EXAMPLE 1

12 g. (0.0132 moles) of leurosine sulfate are dissolved in 2640 ml. of acetone, thereafter 0.6 l. of glacial acetic acid, freshly distilled from a mixture containing chromic acid, are added. The solution is cooled to $-55°$ C., and cold acetic anhydride, containing 5.94 g. (0.135 moles) of chromic acid, are added to the stirred mixture within 3 minutes. The mixture is left to stand for further five minutes, then the pH of the solution is adjusted to 6 using cold concentrated aqueous ammonia. This operation is carried out within 7 minutes, and requires about 6 l. of ammonia solution. During this neutralization the mixture is cooled in order to prevent the temperature from rising above $+50°$ C. The obtained mixture is filled into a glass vessel equipped with a glass stirrer and an outlet tap, which already contains 9 l. of distilled water. The diluted solution is rendered alkaline with further amounts of aqueous ammonia, to set pH=8.5.

Thereafter the reaction mixture is extracted with 4×1.5 l. of methylene chloride. The alkaloid bases are transferred into the methylene chloride phase. The phases are separated, the organic solutions are combined, and washed with 3×1 l. of distilled water for removing ammonium acetate formed in the neutralization step. Thereafter the organic phase is dried over sodium sulfate, and evaporated to dryness under reduced pressure.

10 g. of a beige-white dry residue are obtained; the product is a crude mixture of N-formyl-leurosine and N-demethyl-leurosine.

The dry residue is dissolved in 60 ml. of benzene, and the solution is poured onto a chromatographic column with a diameter of 35 mm., filled with 500 g. of aluminium oxide (IV-V activity grade). The filling is prepared from a benzene suspension of aluminum oxide.

The column is eluted with the solvents or solvent mixtures listed in Table 1.

TABLE 1

| Composition of eluting agent | Amount of eluting agent ml. |
| --- | --- |
| Benzene | 900 |
| 9:1 mixture of benzene and chloroform | 1800 |
| 8.5:1.5 mixture of benzene and chloroform | 1000 |
| 8:2 mixture of benzene and chloroform | 2800 |
| 1:1 mixture of benzene and chloroform | 2800 |
| Chloroform | 800 |

The effluent is collected into fractions each of 400 ml. volume. The various fractions are examined by thin layer chromatography (Fransworth, N. R. et al.: Lloydia, 27, 302 [1964]).

Fractions 1 to 5 do not contain alkaloids. The first traces of alkaloid appear generally in fraction 6, which contains mainly unreacted leurosine. N-demethyl-leurosine generally appears first around fraction 7, and is eluted completely until about fraction 15. The elution of N-formyl-leurosine starts at about fraction 13, and terminates generally around fractions 19-21.

The fractions which, on the basis of thin layer chromatographical analysis, contain the same alkaloids are combined, and evaporated to dryness under reduced pressure.

5.6 g. of crude, amorphous N-formyl-leurosine and 1.5 g. of crude, amorphous N-demethyl-leurosine are obtained.

In the next step these crude, amorphous bases are converted separately into their monosulfates. One part by weight of the crude product is dissolved in 5 part by volume of dry ethanol, thereafter the solution is acidified to pH 4 by adding an 1 percent sulfuric acid solution in dry ethanol. The separation of the crystalline sulfate starts immediately. The mixture is allowed to stand at room temperature for several hours, and then the separated crystals are filtered off. The salts are then recrystallized as follows: one part by weight of the crystalline sulfate is dissolved in 5 parts by volume of methanol, and the volume of the solution is increased to five-fold with dry ethanol. The solution is allowed to stand at room temperature, then the separated product is filtered off, washed with dry ethanol, and dried.

In this process the following substances are obtained: 4.8 g. (40.1%) of N-formyl-leurosine monosulfate, m.p.: 248-252° C. (Boetius), $(\alpha)_{20}{}^D = +37°$ (c=1, in water); and 1.1 g. (9.3%) of N-demethyl-leurosine monosulfate; decomposes without melting; $(\alpha)_{20}{}^D = 3.2°$ (c=1, in water).

In order to determine the physical constants of the N-formyl-leurosine base, a part of the thus-obtained N-formyl-leurosine monosulfate is dissolved in water, the pH of the solution is adjusted to 8 to 9 with concentrated aqueous ammonia, and the mixture is extracted three times with methylene chloride. The organic phases are combined, dried and evaporated to dryness under reduced pressure. The obtained amorphous N- formyl-leurosine is recrystallized from methanol. The crystalline N-formyl-leurosine melts at 209°–211° C. (Boetius); $(\alpha)_{20}{}^D = +80.3°$ (c=1, in chloroform).

The IR spectrum of N-formyl-leurosine is shown in FIG. 2. This spectrum is different from that of leurosine in the strong absorption band of the formyl group, which appears at 1672 $cm^{-1}$.

On the basis of the mass spectrum, the mass number of the N-formyl-leurosine molecule ion is 822. The measured exact mass is M=822.3977, from which the empirical formula $C_{46}H_{54}N_4O_{10}$, with the theoretical mass of 822.39o09, can be calculated.

Analysis: Calculated for $C_{46}H_{54}N_4O_{10}$: C: 67.15%, H: 6.61%, N: 6.81%, O: 19.43%. Found: C: 66.95%, H: 6.58%, N: 6.75%, O: 19.27%.

This molecule ion gives rise to an ion peak with mass number 793, corresponding to the removal of the formyl group, as is proved by the exact mass $m/e_{measured} = 793.3866$.

The empirical formula corresponding to this mass number is $C_{45}H_{53}N_4O_9$, with a calculated mass of $m/e_{calculated} = 793.3862$.

Similarly to the mass spectrum of the leurosine base, the ion peak corresponding to mass number 353 also appears in the mass spectrum of the N-formyl-leurosine base, which corresponds to the epoxyvelbanamine moiety. This fact has also been proved by the measurement of the exact mass: $m/e_{measured} = 353.1874$, which corresponds to the empirical formula of $C_{21}H_{25}N_2O_3$, with a calculated mass of $m/e_{calculated} = 353.1858$.

In order to determine the physical constants of the N-demethyl-leurosine base, N-demethyl-leurosine monosulfate is dissolved in water, the pH of the solution is adjusted to 8 to 9 with aqueous ammonia, and the liberated base is extracted with methylene chloride. The organic phases are combined, dried and evaporated to dryness. The amorphous, dry residue is recrystallized from methanol.

Crystalline N-demethyl-leurosine has the following physical constants: m.p.: 208°–210° C. (Boetius); $(\alpha)_{20}{}^D = +50.1°$ (c=1, in chloroform).

The IR spectrum of N-demethyl-leurosine is given in FIG. 3. This spectrum is different from that of leurosine in the strong absorption band of the secondary amine group, formed upon demethylation, appearing at 3350 $cm^{-1}$.

On the basis of the mass spectrum, the mass number of the N-demethyl-leurosine molecule is 794. From the exact mass number given below, the empirical formula $C_{45}H_{54}N_4O_9$ can be calculated.

Analysis: Calculated for $C_{45}H_{54}N_4O_9$: C: 68.00%, H: 6.85%, N: 7.05%, O: 18.10%. Found: C: 67.85%, H: 6.79%, N: 6.90%, O: 17.95%.

Measured mass $m/e_{measured} = 794.3895$.

On the basis of the above formula $m/e_{calculated} = 794.3882$.

EXAMPLE 2

1 g. of N-demethyl-leurosine is dissolved in the mixture of 6 ml. of concentrated formic acid and 1 ml. of acetic anhydride, and the mixture is left to stand at room temperature for 10 minutes. Thereafter the mixture is poured into 30 ml. of cold (0° to 5° C.) water, and the pH of the mixture is adjusted to 9.0 with cold, concentrated aqueous ammonia. The ammonia solution is added under stirring. The alkaloid is extracted from the aqueous solution with 3×30 ml. of methylene chloride. The methylene chloride solutions are combined, dried and evaporated to dryness under reduced pressure.

0.95 g. of amorphous, white N-formyl-leurosine are obtained, which is converted into its monosulfate as described in Example 1. In this reaction 1.01 g. of N-formyl-leurosine monosulfate are obtained.

EXAMPLE 3

10 g. of a beige-white, foam-like crude residue consisting of N-formyl-leurosine and N-demethyl-leurosine obtained by oxidizing 12 g. (0.0132 moles) of leurosine sulfate as described in Example 1 are dissolved in a mixture of 60 ml. of concentrated formic acid and 10 ml. of acetic anhydride, and the mixture is poured, under stirring into 300 ml. of cold (0° to 5° C.) water. The pH of the mixture is adjusted to 9.0 with cold, concentrated aqueous ammonia, under stirring. The solution is extracted with 3×100 ml. of methylene chloride. The methylene chloride phases are combined, dried, and evaporated to dryness under reduced pressure. 9.8 g. of amorphous, white, crude N-formyl-leurosine are obtained.

The obtained crude N-formyl-leurosine is purified by column chromatography. The crude product is dissolved in 60 ml. of benzene, and this solution is charged onto a column of 45 mm. diameter, filled with 500 g. of aluminium oxide (III activity grade) in benzene. The column is eluted with the solvents listed in Table 2.

TABLE 2

| Composition of the eluting agent | Amount of the eluting agent, ml. |
|---|---|
| Benzene | 1200 |
| 2:1 mixture of benzene and chloroform | 5000 |
| 1:1 mixture of benzene and chloroform | 3000 |
| Chloroform | 800 |

The effluent is collected into fractions each of 400 ml. volume.

Fractions 1 to 3 do not contain alkaloids. Fractions 4 to 10 contain the accompanying materials. Starting at about fraction 11, N-formyl-leurosine also appears in addition to the accompanying substances. Approximately fractions 15 to 20 contain N-formyl-leurosine alone. In the subsequent fractions the amount of eluted N-formyl-leurosine gradually decreases. The fractions which contain N-formyl-leurosine alone are combined and evaporated to dryness under reduced pressure. 6.5 g. of crude, amorphous N-formyl-leurosine are obtained.

This crude, amorphous N-formyl-leurosine base is converted into its monosulfate as follows: 6.5 g. of N-formyl-leurosine are dissolved in 32.5 ml. of dry ethanol, thereafter the solution is acidified to pH 4 by adding a 1% sulfuric acid solution in dry ethanol. The separation of the crystalline substance starts immediately. The mixture is left to stand at room temperature for several hours, thereafter the crystals are filtered off and washed with dry ethanol. 6.5 g. of crystalline N-formyl-leurosine monosulfate are obtained.

The eluates collected before and after the fractions containing pure N-formyl-leurosine contain accompanying substances and N-formyl-leurosine. These fractions are combined and evaporated to dryness. The amorphous substance (1.75 g.) obtained this way is dissolved in benzene, and purified by chromatography as described above, with the only difference that in order to ensure a better separation the column is eluted with 1200 ml. of a 2:1 mixture of benzene and chloroform. The fractions containing N-formyl-leurosine alone are processed as described above, to yield a further 1.05 g. of pure, crystalline N-formyl-leurosine monosulfate. Total yield: 7.10 g. (63.7%) of N-formyl-leurosine monosulfate. The physical constants of this compound are identical with those given in Example 1.

What we claim is:

1. A compound of the formula I in a dosage form effective for treating lymphoid leukemia in a dosage of 0.3 to 5.0 mg/kg:

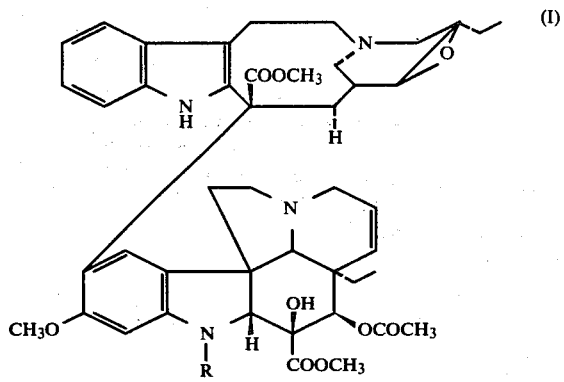

wherein R stands for formyl, or a pharmaceutically acceptable acid addition salt thereof, in pure crystalline form.

2. N-formyl-leurosine monosulfate in a dosage form effective for treating lymphatic leukemia in a dosage form of 0.3 to 5.0 mg/kg and in pure crystalline form.

* * * * *